United States Patent
Omohundro et al.

(10) Patent No.: US 11,022,169 B2
(45) Date of Patent: Jun. 1, 2021

(54) DISPOSABLE ROTARY FLEXIBLE DRIVESHAFT AND SURGICAL CUTTER

(71) Applicant: Med X Composites, LLC, Minden, NV (US)

(72) Inventors: Thomas W. Omohundro, Minden, NV (US); C. Peter Darby, Gardnerville, NV (US)

(73) Assignee: Med X Composites, LLC, Minden, NV (US)

( * ) Notice: Subject to any disclaimer, the term of this patent is extended or adjusted under 35 U.S.C. 154(b) by 311 days.

(21) Appl. No.: 15/913,492

(22) Filed: Mar. 6, 2018

(65) Prior Publication Data

US 2018/0258979 A1 Sep. 13, 2018

Related U.S. Application Data

(60) Provisional application No. 62/467,876, filed on Mar. 7, 2017.

(51) Int. Cl.
| | |
|---|---|
| *A61B 17/16* | (2006.01) |
| *F16C 1/08* | (2006.01) |
| *F16C 1/06* | (2006.01) |
| *F16C 1/26* | (2006.01) |
| *A61B 17/00* | (2006.01) |

(52) U.S. Cl.
CPC ............ *F16C 1/08* (2013.01); *A61B 17/1631* (2013.01); *A61B 17/1633* (2013.01); *F16C 1/06* (2013.01); *F16C 1/26* (2013.01); *F16C 1/262* (2013.01); *A61B 2017/0023* (2013.01); *A61B 2017/0046* (2013.01); *A61B 2017/00473* (2013.01)

(58) Field of Classification Search
CPC .... F16C 1/08; F16C 1/26; F16C 1/262; F16C 1/06; A61B 17/1633; A61B 17/1631; A61B 2017/00473; A61B 2017/0046; A61B 2017/0023
USPC .................. 464/52, 53, 57, 58, 60; 606/180
See application file for complete search history.

(56) References Cited

U.S. PATENT DOCUMENTS

| | | | |
|---|---|---|---|
| 2,706,417 A * | 4/1955 | Waner | D07B 1/0673 464/60 |
| 4,260,143 A | 4/1981 | Kliger | |
| 5,108,411 A | 4/1992 | McKenzie | |
| 5,490,860 A | 2/1996 | Middle et al. | |
| 5,803,812 A * | 9/1998 | Kakiuchi | F16C 1/02 464/58 |

(Continued)

FOREIGN PATENT DOCUMENTS

EP    3 646 804 A3    7/2020

OTHER PUBLICATIONS

Extended European Search Report dated Jun. 23, 2020 for European Patent Application No. 19 20 22903 (11 pages).

*Primary Examiner* — Greg Binda
(74) *Attorney, Agent, or Firm* — Taylor IP, P C,

(57) ABSTRACT

A flexible driveshaft includes a proximal coupler and a distal coupler each configured to couple to a respective component of an instrument, and a flexible shaft having a proximal end connected to the proximal coupler, a distal end connected to the distal coupler, and a longitudinal axis. The flexible shaft may include a sleeve, and a core having a first end and a second end. The core is housed within the sleeve. The flexible shaft also includes a plurality of coils arranged around the longitudinal axis in at least one layer.

42 Claims, 4 Drawing Sheets

(56) References Cited

U.S. PATENT DOCUMENTS

| | | | |
|---|---|---|---|
| 5,816,923 A * | 10/1998 | Milo | A61B 17/320758 |
| | | | 464/58 |
| 5,849,023 A | 12/1998 | Mericle | |
| 6,078,010 A * | 6/2000 | Funahashi | F16C 1/20 |
| 6,332,886 B1 | 12/2001 | Green et al. | |
| 6,443,973 B1 | 9/2002 | Whitman | |
| 7,407,440 B2 | 8/2008 | White | |
| 7,523,924 B2 * | 4/2009 | Melancon | E04C 5/02 |
| | | | 267/166 |
| 8,366,559 B2 | 2/2013 | Papenfuss et al. | |
| 8,960,519 B2 | 2/2015 | Whitman et al. | |
| 9,603,983 B2 * | 3/2017 | Roehn | A61M 1/1034 |
| 10,022,131 B1 | 7/2018 | Burley et al. | |
| 10,631,879 B2 * | 4/2020 | Omohundro | A61B 17/1633 |
| 2009/0243174 A1 | 10/2009 | Spencer et al. | |
| 2012/0172905 A1 * | 7/2012 | Lee Shee | A61B 17/32002 |
| | | | 606/180 |
| 2015/0342619 A1 | 12/2015 | Weitzman | |
| 2016/0030072 A1 | 2/2016 | Devlin et al. | |
| 2016/0310209 A1 | 10/2016 | Parihar et al. | |
| 2017/0007272 A1 | 1/2017 | Weitzman et al. | |
| 2018/0258979 A1 | 9/2018 | Omohundro et al. | |

* cited by examiner

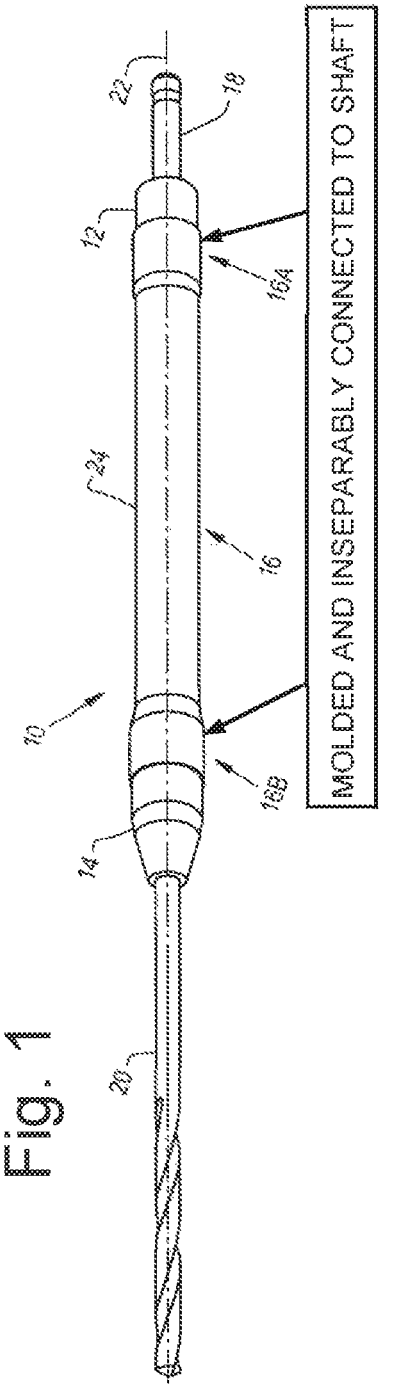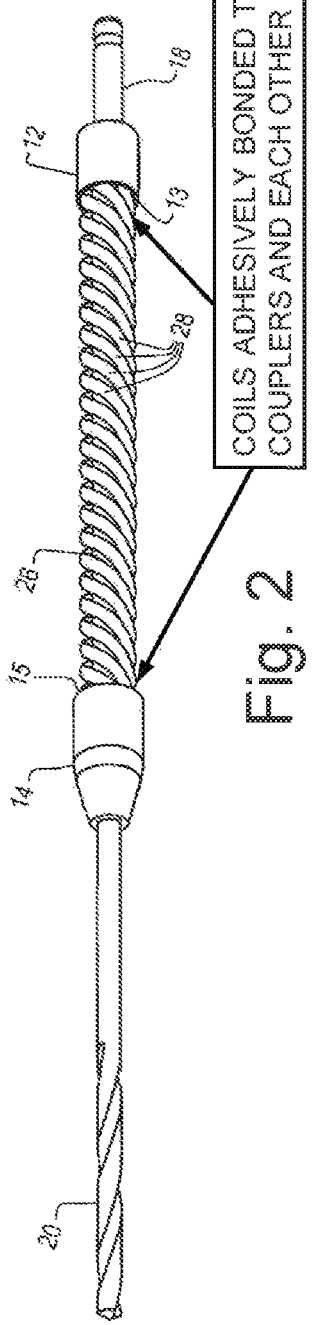
Fig. 1
Fig. 2

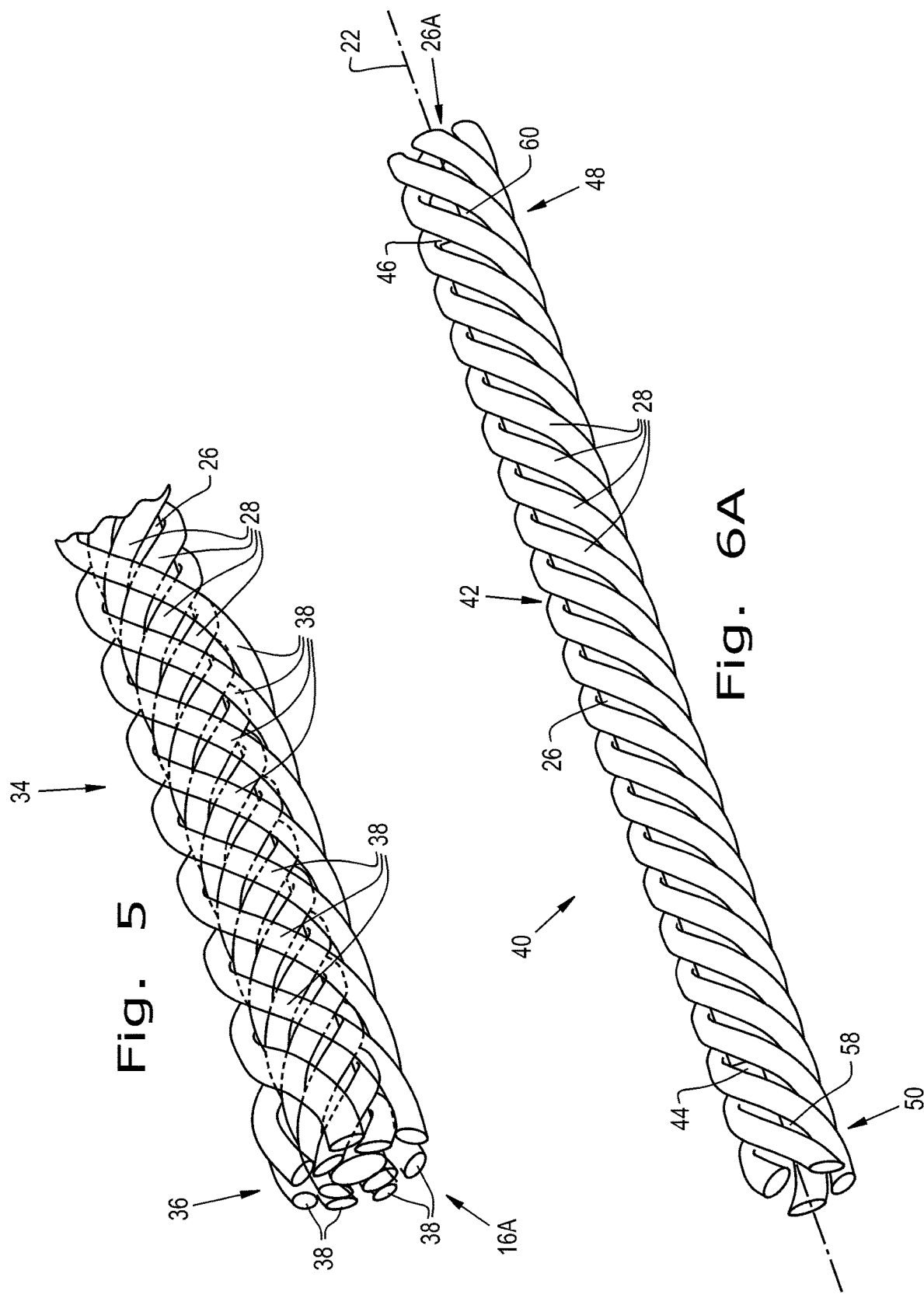

DISPOSABLE ROTARY FLEXIBLE DRIVESHAFT AND SURGICAL CUTTER

CROSS REFERENCE TO RELATED APPLICATIONS

This is non-provisional application based upon U.S. provisional patent application Ser. No. 62/467,876, entitled "SINGLE USE FLEXIBLE DRIVESHAFT", filed Mar. 7, 2017, which is incorporated herein by reference.

BACKGROUND OF THE INVENTION

1. Field of the Invention

The present invention relates to driveshafts, and, more particularly, to a disposable flexible driveshaft.

2. Description of the Related Art

In surgical operations, it is often advantageous to use a surgical instrument with a flexible shaft, especially when the pathway from the power source to the driven part is obstructed. The flexible shaft circumvents the obstruction while still providing the necessary transmission of force between two components of a surgical instrument. The transmission of force includes both rotary torque and axial force; yet, the primary function of a flexible shaft is to transmit rotary motion in a curvilinear manner. Generally, flexible shafts include a deformable, rotating shaft and a pair of end fittings for respectively attaching the power source and the driven tool of the surgical instrument. For example, a flexible shaft may connect a drill to the tool head for the drilling or reaming of curved bones.

It is well known in the art to use wound springs over a central drive core or a hollow core to form flexible shafts. U.S. Pat. No. 5,108,411 discloses a catheter with a flexible shaft that has an internal drive cable for rotating a work element at the distal end of the catheter. However, such prior art designs which incorporate wound metal springs suffer from sanitation and reusability issues. Predominantly, cleaning and sterilization of the springs is taxingly laborious as blood and debris often becomes lodged within the windings of the springs. Subordinately, spring designs also suffer from unwinding or performance loss as they are rotated in the reverse direction. In order to combat the issues of unwinding, many spring designs incorporated a second, subsidiary spring, which was wound in the opposite direction and disposed within the primary spring. Although the issues of unwinding were waned, the sanitation concerns escalated as the disposition of the subsidiary spring within the primary spring rendered cleaning effectively unreasonable.

As an alternative to the coil spring design, a metallic tubing, wire, or rod may be used to form the flexible driveshaft. It is also known to incorporate a helix structure to ensure the requisite axial flexibility and torsional rigidity of the shaft. Some prior art designs use super-elastic metals, such as U.S. Pat. Nos. 5,488,761, and 7,407,440 which uses a nitinol (nickel-titanium) tubing as the body of its shaft. These devices overcome some of the pitfalls of the coil spring design with respect to sanitation and reusability. However, because the prior art metallic tubing, wire, or rod designs are expensive to manufacture they must be reused in order to be cost effective. Therefore, the cost of re-sterilization at the work site or hospital cannot be avoided.

What is needed in the art is a flexible driveshaft that is cost-effective and avoids the protracted cost of sanitation after each use.

SUMMARY OF THE INVENTION

The present invention provides a low-cost, flexible driveshaft that can be disposed of after a single or relatively few uses without sacrificing the requisite balance of lateral stiffness and torsional strength in order to facilitate the transmission of rotary power to a surgical tool.

In accordance with an embodiment of the present invention, a flexible driveshaft includes a proximal coupler and a distal coupler each configured to couple to a respective component of an instrument, and a flexible shaft. The flexible shaft includes a proximal end connected to the proximal coupler, a distal end connected to the distal coupler, and a longitudinal axis. The flexible shaft also includes a sleeve and a core having a first end and a second end. The core is housed within the sleeve. The flexible shaft further includes a plurality of coils arranged around the core in at least one layer, wherein the flexible driveshaft is configured to be disposable after a single or relatively few uses.

In accordance with another embodiment of the present invention, a flexible driveshaft includes a flexible shaft having a proximal end and a distal end, each configured to couple to a respective component of a tool. The flexible shaft has a longitudinal axis, and includes a core having a first end and a second end. The flexible shaft also includes a plurality of coils arranged around the core in at least one layer.

In accordance with another embodiment of the present invention, a flexible shaft assembly includes a plurality of coils arranged in at least one layer about a longitudinal axis. The plurality of coils forms a hollow flexible shaft having a proximal end and a distal end. The proximal and distal ends are configured to couple with respective components of a tool.

An advantage of the present invention is that flexible driveshafts and flexible shafts can be cost effectively disposed of after a single or relatively few uses while still maintaining the requisite axial flexibility and torsional rigidity.

BRIEF DESCRIPTION OF THE DRAWINGS

The above-mentioned and other features and advantages of this invention, and the manner of attaining them, will become more apparent and the invention will be better understood by reference to the following description of an embodiment of the invention taken in conjunction with the accompanying drawings, wherein:

FIG. 1 is a perspective view of an embodiment of a flexible driveshaft, coupled to a tool of a surgical instrument, according to an embodiment of the present invention;

FIG. 2 is a perspective view illustrating the flexible driveshaft of FIG. 1 with the absence of the sleeve covering the flexible shaft, according to an embodiment of the present invention;

FIG. 5 is a perspective view of an end of the flexible shaft of FIG. 3, with an additional layer of coils spirally-arranged around the core, according to an embodiment of the present invention; and FIG. 6A is a perspective view of a flexible driveshaft, according to another embodiment of the present invention;

Corresponding reference characters indicate corresponding parts throughout the several views. The exemplification set out herein illustrates an embodiment of the invention, in one form, and such exemplification is not to be construed as limiting the scope of the invention in any manner.

DETAILED DESCRIPTION OF THE INVENTION

Figure 3:
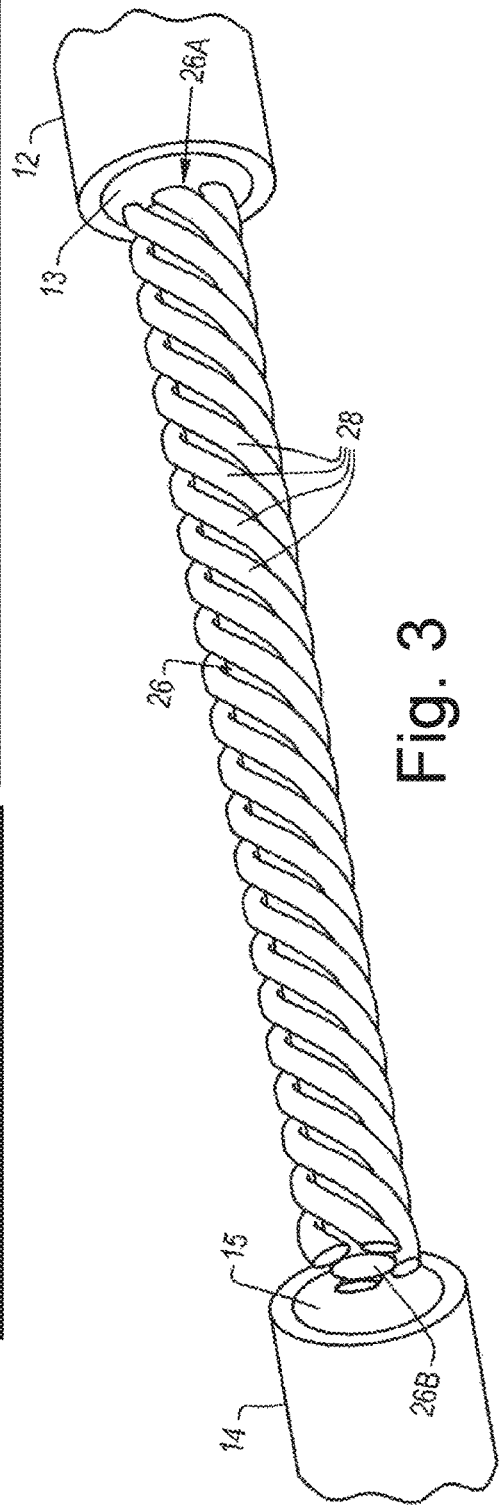
FIG. 3 is a perspective view illustrating the core and coils of the flexible shaft of FIG. 1, to be coupled to the proximal and distal couplers, according to an embodiment of the present invention.

The terms "proximal" and "distal" are used principally throughout this specification for convenience; but it is to be understood that these terms are not intended to be limiting. Thus "proximal" in this specification refers to the feature of the apparatus closest to the operator during use, and "distal" refers to the end of the apparatus farthest from the operator during use.

Referring now to the drawings, and more particularly to FIG. 1, there is shown a flexible driveshaft 10 according to an embodiment of the present invention. The flexible driveshaft 10 includes a proximal coupler 12, a distal coupler 14, and a flexible shaft 16 therebetween. The flexible driveshaft 10 facilitates the drilling of holes in difficult-to-access areas, and it may be manufactured inexpensively enough to be disposable after a single or relatively few uses. The flexible driveshaft 10 may be incorporated as either an element of a one-piece disposable device, or a disposable component of a modular assembly.

For example, the proximal coupler 12, the distal coupler 14 and the flexible shaft 16 may be separate components of the flexible driveshaft 10 of a modular assembly, according to one embodiment of the present invention. In an embodiment of the present invention, the proximal coupler 12 and distal coupler 14 are manufactured from metal, plastic or a composite, and the proximal coupler 12 and distal coupler 14 are removably-connected to the flexible shaft 16 (i.e., to a proximal end 16A and a distal end 16B, respectively, of the flexible shaft 16) such that the flexible shaft 16 is disposable after a single or relatively few uses. Alternatively, the proximal coupler 12 and the distal coupler 14 may be integral, inseparable components of the flexible shaft 16, such that the flexible driveshaft 10 forms a one-piece unit that is disposable after a single or relatively few uses, according to another embodiment of the present invention. In an embodiment of the present invention, the proximal coupler 12 and the distal coupler 14 are each formed of a molded adhesive that are inseparably connected (e.g., bonded) to the flexible shaft 16 (i.e., to the proximal end 16A and the distal end 16B, respectively, of the flexible shaft 16) such that the flexible driveshaft 10 is disposable. Other embodiments of disposable flexible driveshafts and disposable flexible shafts having no couplers are described further below in conjunction with FIGS. 6A-6E.

The proximal and distal couplers 12, 14 attach respective components of a surgical instrument, or components of other types of tools. By way of an exemplary embodiment, the proximal and distal couplers 12, 14 are shown respectively to be in the form of a drive coupler and cutting tool collet. The couplers 12, 14 respectively attach to a power drive attachment 18 and a surgical cutter 20 of a surgical instrument. The power drive attachment 18 is configured to attach to a power source (not shown) which will rotate the flexible shaft 16 and likewise the surgical cutter 20 in order to facilitate the drilling of a bone. The power drive attachment 18 may connect to a motor, a drill, or a handle. The surgical cutter 20 is shown to be a drill bit, but it may be in the form of various interchangeable tools including a reaming head, a screw, a pump, or any other desired orthopedic tool. The proximal and distal couplers 12, 14 can be made of any metal, composite plastic, or adhesive suitable for use with surgical instruments and need not be formed as separate elements, but rather may be formed integrally with the proximal end 16A and the distal end 16B, respectively, of the flexible shaft 16.

Referring now to FIGS. 1-2 collectively, there is shown the flexible shaft 16 which includes the proximal end 16A, the distal end 16B, and a longitudinal axis 22, according to an embodiment of the present invention. The proximal and distal ends 16A, 16B of the flexible shaft 16 connect respectively to the proximal and distal couplers 12, 14 via any known means in the art, including adhesives and/or fasteners. The flexible shaft 16 further includes a sleeve 24, a core 26, and a plurality of coils 28 that are wrapped around the core 26. In one embodiment, the plurality of coils 28 are formed about the core 26 in a counterclockwise direction when the core 26 is viewed from the proximal end 16A, for when the power drive attachment 18 is configured to rotate the flexible shaft 16 in a clockwise direction for proper operation of the tool 20, and the plurality of coils 28 are formed about the core 26 in a clockwise direction when the core 26 is viewed from the proximal end 16A, for when the power drive attachment 18 is configured to rotate the flexible shaft 16 in a counterclockwise direction for proper operation of the tool 20.

The sleeve 24 covers and protects the core 26 and coils 28 of the flexible shaft 16. The sleeve 24 also provides a measure of stiffness such that the when the flexible driveshaft 10 is rotated in the reverse direction it does not succumb to the pitfalls of unwinding or performance loss. In the present embodiment, the sleeve 24 is manufactured of a thin plastic material such that it can be shrink-fit onto the flexible shaft 16. However, the sleeve 24 may be made of any suitable plastic, metal, or composite material, and may be affixed to the couplers 12, 14 by adhesives and/or fasteners. The sleeve 24 may directly abut against the couplers 12, 14, or the sleeve 24 may extend over and onto a respective portion of the couplers 12, 14.

Referring now to FIGS. 2-5 collectively, there is shown in more detail core 26 and the coils 28 which are arranged around the core 26, according to an embodiment of the present invention. The core 26 of the flexible shaft 16 is housed within the sleeve 24, and the respective ends 26A, 26B of the core 26 connect to the proximal coupler 12 and the distal coupler 14. The couplers 12, 14 may include mating bores 13, 15 such that the ends 26A, 26B of the core 26 fit therein. The core 26 in the present embodiment is made from a nylon rod, which is lightweight and cost effective to manufacture. However, the core 26 may be made of any suitable plastic, metal, or composite material that enables the flexible shaft 16 to be cost effectively manufactured. The core 26 may be a solid member or optionally a cannulated member (e.g., including a through-hole 30 coincident with the longitudinal axis 22 of the flexible shaft 16, formed to facilitate a pathway for removal of any material dislodged by the tool (e.g., bone or tissue dislodge by the cutter 20, or by any other orthopedic tool, such as a reaming head)).

Figure 4:
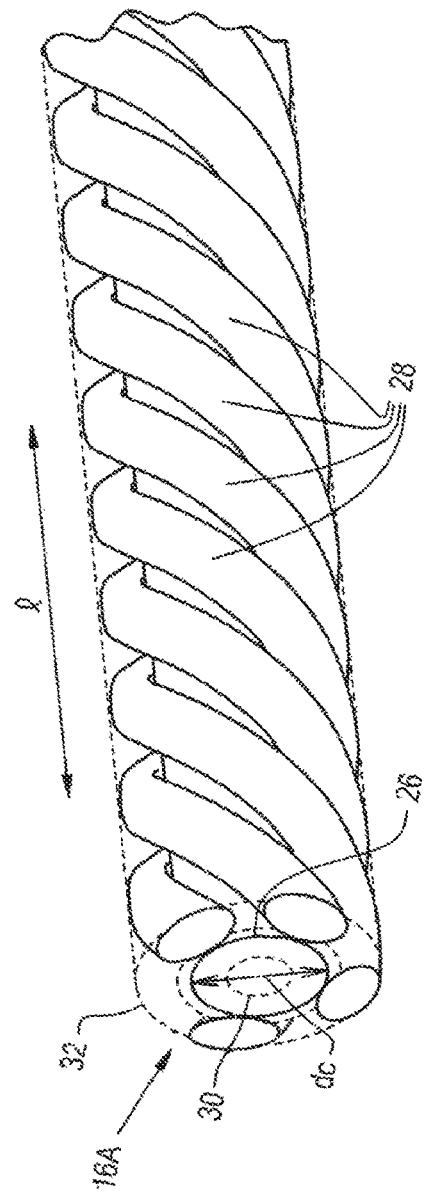
FIG. 4 is a perspective view of an end of the flexible shaft of FIG. 3, with an optional polymer resin, according to an embodiment of the present invention.

In one embodiment, the coils 28 are formed of a fiber-reinforced plastic composite, such as continuous fiberglass-reinforced epoxy resin composite helixes. Alternatively, the coils 28 are formed of other commercial reinforcing fibers, resin matrix materials, or metal wire such as stainless steel or plastic-coated carbon steel. The coils 28 may be arranged about the core 26. The scope of the invention covers coils that are separated from one another and coils embedded in a resin. In another embodiment, the fiber-reinforced plastic composite may be molded to form the coils 28. The coils 28 may also be referred to as a roving, such as a multi-strand fiberglass roving. The coils 28 may also be formed of fibers, for example, glass fibers, carbon fibers, or aramid fibers, that are spirally-arranged about the core 26. As mentioned above, the coils 28 may optionally be embedded in a polymer matrix such as an epoxy resin, an ester, a polyimide, a polypropylene, or any other known material in the art. For example, and as illustrated in FIG. 4, the coils 28 are embedded in a polymer matrix 32, according to an embodiment of the present invention. In one embodiment of the present invention, the coils 28 are spiral-formed fiberglass roving embedded in an epoxy resin.

In one embodiment, the angular orientation of the coils 28 relative to the longitudinal axis 22 of the flexible shaft 16 is approximately 45°, however the scope of the present invention covers the coils 28 having any helix angle with respect to the longitudinal axis 22. In one embodiment of the invention, and as illustrated by FIG. 4, a distance 1 between the same circumferential position of consecutive locations of a single coil (i.e., the helical pitch) is in the range of 18 to 25 mm for the flexible shaft 16 having an outside diameter of 7.5 mm, however the scope of the present invention covers other helical pitches with the same or with different shaft diameters.

FIGS. 2-4 show four coils arranged in a single layer (i.e., a quadruple helix), according to one embodiment of the invention; however, there may be less or more coils arranged around the core 26 according to other embodiments of the invention.

Additionally, there may be multiple layers of coils 28 wrapped around the core 26. For example, FIG. 5 shows the core 26 and two layers of coils 34, 36 which are spirally-arranged (i.e., spiral-formed) around the core 26, according to another embodiment of the present invention. In this embodiment, the flexible shaft 16 (FIG. 1) includes the core 26, a first layer 34 of coils 28 formed from four coils, and a second layer 36 of coils. In one embodiment, the number of coils 38 of the second layer 36 is selected such that the circumferential distance between adjacent coils 38 of the second layer 36 are approximately equal to the circumferential distance between adjacent coils 28 of the first layer 34. For illustration purposes only, the second layer 36 is formed from seven coils. Only a portion of the second layer 36 of coils 38 is shown for ease of illustration. For conventional operation of the flexible driveshaft 16 (i.e., clockwise rotation when viewed from the proximal end 16A), the first layer 34 of coils 28 are wrapped around the core 26 in a clockwise sense when the core 26 is viewed from a perspective of the proximal end 16A (also referred to as a right-hand rotation of the coils or right-handedness), and the second layer 36 of coils 38 are wrapped around the core 26 in a counterclockwise sense when the core 26 is viewed from the perspective of the proximal end 16A (also referred to as left-hand rotation of the coils or left handedness). However, the scope of the present invention covers any number of layers, any number of individual coils forming each of the respective layers, and any combination of handedness of the respective layers.

In one embodiment of the present embodiment, the coils 28 are adhesively bonded at each end to the couplers 12, 14 and to each other. However, in another embodiment of the present invention, the coils 28 may be secured to the couplers 12, 14 by fasteners. The arrangement of the coils 28 wrapped around the core 26 creates a desired balance of the lateral stiffness and torsional strength sufficient for the flexible shaft 16 to push and rotate a tool, such as the surgical cutter 20, when the flexible driveshaft 10 is bent.

FIG. 6A shows a flexible driveshaft 40 according to an embodiment of the present invention. The flexible driveshaft 40 includes a flexible shaft 42 having a longitudinal axis 22, a core 26 having a first end 44 and a second end 46, and a plurality of coils 28 spirally-arranged around the core 26 in at least one layer. The plurality of fibers 28 may be arranged as one or more cylindrical layers. The core and the cylindrical layers are arranged concentrically about the longitudinal axis 22. The flexible driveshaft 40 is similar to the flexible driveshaft 10 in that the flexible driveshaft 40 facilitates the drilling of holes in difficult-to-access areas, and it may be manufactured inexpensively enough to be disposable after a single or relatively few uses.

However, in contrast to the flexible driveshaft 10, the flexible driveshaft 40 does not include proximal and distal couplers. The flexible shaft 42 of the flexible driveshaft 40 includes a proximal end 48 and a distal end 50, each configured to couple to respective components of an instrument or tool, such as surgical tools and power drive attachments, via core recesses 58, 60. For example, in one embodiment of the present invention, the proximal end 48 is configured as a drive coupler for coupling with a driver, such as a power drive attachment 52 (FIG. 6C), and the distal end 50 is configured as a tool collet for coupling with a tool, such as a drill bit 54 (FIG. 6B).

Figure 6B:
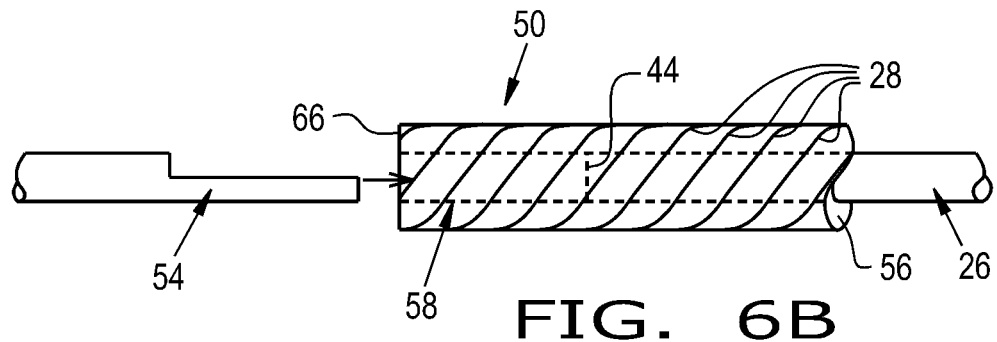
FIG. 6B is a perspective view of a distal end of the flexible driveshaft of FIG. 6A, according to an embodiment of the present invention.
Figure 6C:
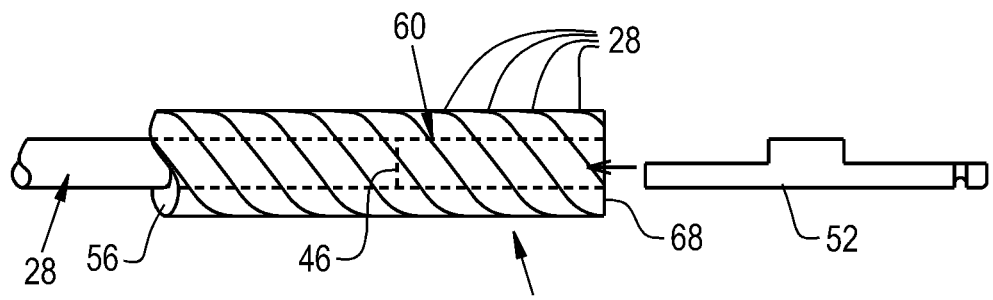
FIG. 6C is a perspective view of a proximal end of the flexible driveshaft of FIG. 6A, according to an embodiment of the present invention.

FIG. 6B and FIG. 6C show the distal end 50 of the flexible shaft 42 and the proximal end 48 of the flexible shaft 42, according to an embodiment of the present invention. As illustrated by FIG. 6B, each coil of the plurality of coils 28 formed of a fiber-reinforced plastic composite 56 or optionally embedded in a polymer resin 56 at the distal end 50 extend beyond the first end 44 of the core 26, thereby forming the distal end core recess 58. Similarly, as illustrated by FIG. 6C, each coil of the plurality of coils 28 formed of the fiber-reinforced plastic composite 56 or optionally embedded in the polymer resin 56 at the proximal end 48 extend beyond the second end 46 of the core 26, thereby forming the proximal end core recess 60. The proximal and distal end core recesses 60, 58 of the proximal and distal ends 48, 50 of the flexible shaft 42 are configured to couple to respective components of a tool, such as a surgical instrument.

Figure 6D:
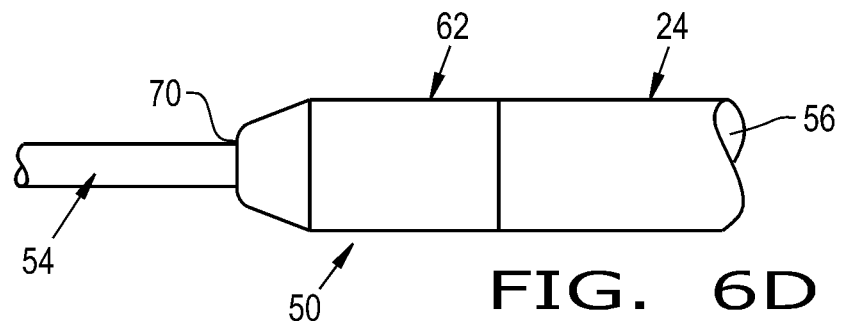
FIG. 6D is a perspective view of the distal end of the flexible driveshaft of FIG. 6B, with an adhesive end coupled to a surgical tool, according to an embodiment of the present invention.
Figure 6E:
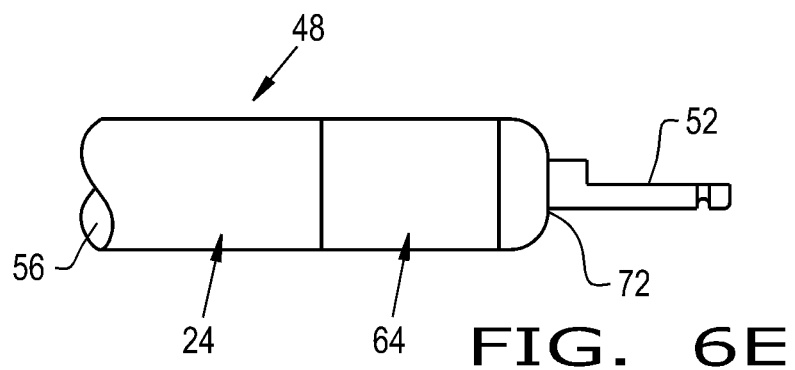
FIG. 6E is a perspective view of the proximal end of the flexible driveshaft of FIG. 6C, with an adhesive end coupled to a drive attachment, according to an embodiment of the present invention.

FIGS. 6D and 6E show the distal end 50 of the flexible shaft 42 and the proximal end 48 of the flexible shaft 42, as illustrated in FIGS. 6B and 6C respectively, according to another embodiment of the present invention. As illustrated by FIG. 6D, the distal end 50 includes a distal molded or cast adhesive end 62 formed either around the plurality of coils 28 at the distal end 50 that extend beyond the first end 44 of the core 26 that form the core recess 58, or bonded with a first end 66 of the plurality of coils 28. Furthermore, and as illustrated by FIG. 6E, the proximal end 48 includes a proximal molded or cast adhesive end 64 formed either around the plurality of coils 28 at the proximal end 48 that extend beyond the second end 46 of the core 26 that form the core recess 60, or bonded with a second end 68 of the plurality of coils 28. In one embodiment of the present invention, the molded or cast adhesive ends 62, 64 are formed as inseparably components completely integrated with the distal and proximal ends 50, 48. In another embodiment of the invention, the molded or cast adhesive ends 62, 64 include respective openings 70, 72 configured to receive respective components of the tool for coupling the components to the respective core recesses 58, 60. Although FIGS. 6D and 6E show the flexible shaft 42 having a sleeve 24 which either abuts against the molded or cast adhesive ends 62, 64 or covers at least a portion of the molded or cast adhesive ends 62, 64, the scope of the present invention covers the FIGS. 6D and 6E embodiments without the sleeve 24, and the FIGS. 6B and 6C embodiments with a sleeve 24 covering at least a portion of the flexible shaft 42.

As illustrated in FIGS. 6A-6E, the coils 28 forming the core recesses 58, 60 are directly coupled to respective components of a tool when such components are inserted into the respective core recesses 58, 60, with or without the molded or cast adhesive ends 62, 64, thereby coupling the flexible driveshaft 40 directly to the power drive attachment 52 and the tool 54 without the use of separate, non-integrated couplers.

In another embodiment of the invention, and referring to FIGS. 6A-6E, a flexible shaft assembly is the flexible shaft 42 without the core 26. The flexible shaft assembly includes the plurality of coils 28 spirally-arranged (e.g., arranged as helixes) in at least one layer about the longitudinal axis 22. In this embodiment, the plurality of coils 28 form a hollow flexible shaft (i.e., said flexible driveshaft 40 without the core 26).

The distal and proximal ends 50, 48 are configured to permanently bond with, or removeable-couple to, a respective component of a tool, such as a shank of a drill, a ream, an abrading tool, a screw driving bit, a collet with the capability to use interchangeable tools or components of tools, or a coupling to attach a pump (not shown). For example, the proximal and distal ends 48, 50 may be configured to permanently bond with a respective component of a tool by use of an adhesive, a fastener, or a weld.

In another embodiment, the proximal and distal ends 48, 50 of the flexible shaft assembly include a proximal adhesive end 64 attached to the proximal end 48 and a distal adhesive end 62 attached to the distal end 50. Although the adhesive ends 62, 64 are configured to removably-couple to respective components of a tool, such as a driver 52 or other components 54 of a tool, via collet-like-formed adhesive ends, for example, the scope of the present invention covers adhesive ends 62, 64 configured to permanently bond with respective components of a tool. In one embodiment, the driver 52 may be any standard stainless steel quick connect or stainless-steel rod with a quick connect shape cast or molded around the rod bonded to the coils 28 at the proximal end 48 and/or bonded to the proximal adhesive end 64. In one embodiment, the adhesive ends 62, 64 are molded or cast.

In other embodiments of the present invention, the dimensions and material of the core 26 and the coils 28 of the flexible driveshaft 10 and the dimensions and material of the core 26 and the coils 28 of the flexible driveshaft 40 are configured to support a compression load, supply up to 9 N-m of torque, and to support up to 90 degrees of bend as measured with respect to the longitudinal axis 22.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims. In addition, this application is intended to cover all combinations of the several embodiments that are consistent with the purpose and functions covered by the overall description within the spirit and scope of the disclosure.

What is claimed is:

1. A flexible shaft assembly, comprising:
   a plurality of coils arranged in at least one layer about a longitudinal axis, said plurality of coils forming a hollow flexible shaft, said hollow flexible shaft having a proximal end and a distal end, said plurality of coils in said at least one layer being separated from one another; and
   a surgical cutter coupled to the distal end of the hollow flexible shaft and configured to be rotated by the hollow flexible shaft to cut tissue.

2. The flexible shaft assembly according to claim 1, wherein each coil of said plurality of coils is formed as a helix.

3. The flexible shaft assembly according to claim 1, wherein each coil of said plurality of coils is formed of a fiber-reinforced plastic composite.

4. The flexible shaft assembly according to claim 1, wherein said plurality of coils comprise a quadruple helix.

5. The flexible shaft assembly according to claim 1, wherein said plurality of coils arranged in said at least one layer comprise a first plurality of coils arranged in a first cylindrical layer and a second plurality of coils arranged in a second cylindrical layer, said first and second cylindrical layers arranged concentrically about said longitudinal axis.

6. The flexible shaft assembly according to claim 1, wherein each coil of said plurality of coils of distal end is permanently bonded with said surgical cutter.

7. The flexible shaft assembly according to claim 6, wherein said each coil of said plurality of coils of said distal end is permanently bonded with said surgical cutter by at least one of an adhesive, a fastener and a weld.

8. The flexible shaft assembly according to claim 1, further comprising a proximal adhesive end integrated with said proximal end and a distal adhesive end integrated with said distal end.

9. The flexible shaft assembly according to claim 8, wherein said each adhesive end is a molded or cast adhesive end.

10. The flexible shaft assembly according to claim 1, further comprising a core, said core concentric with said longitudinal axis, and said plurality of coils arranged about said core.

11. The flexible shaft assembly according to claim 10, wherein said core has a first end and a second end, and wherein said distal end extends beyond said first end forming a first core recess and said proximal end extends beyond said second end forming a second core recess.

12. The flexible shaft assembly according to claim 1, further comprising a sleeve, wherein said sleeve is arranged around said hollow flexible shaft.

13. The flexible shaft assembly according to claim 12, wherein said sleeve is shrunk-fit onto said hollow flexible shaft.

14. A flexible driveshaft assembly, comprising:
a flexible shaft having a proximal end and a distal end, said flexible shaft having a longitudinal axis, said flexible shaft comprising:
a core having a first end and a second end; and
a plurality of coils arranged around said core in at least one layer, said plurality of coils in said at least one layer being separated from one another; and
a surgical cutter coupled to the distal end of the flexible shaft and configured to be rotated by the flexible shaft to cut tissue.

15. The flexible driveshaft assembly of claim 14, wherein said core comprises a non-metallic core.

16. The flexible driveshaft assembly of claim 14, wherein said core comprises a hollow core.

17. The flexible driveshaft assembly of claim 14, wherein said plurality of coils are spiral-formed multi-strand fiberglass roving.

18. The flexible driveshaft assembly of claim 14, wherein said plurality of coils are embedded in a polymer matrix.

19. The flexible driveshaft assembly according to claim 14, wherein each coil of said plurality of coils is formed of a fiber-reinforced plastic composite.

20. The flexible driveshaft assembly of claim 14, wherein an orientation of said coils relative to said longitudinal axis of said flexible shaft is approximately 45°.

21. The flexible driveshaft assembly of claim 14, wherein said flexible shaft further comprises a sleeve, said sleeve shrunk-fit onto said core and said plurality of coils arranged around said core.

22. The flexible driveshaft assembly of claim 14, wherein each of said proximal end and said distal end comprise a core recess.

23. The flexible driveshaft assembly of claim 22, wherein each of said proximal end and said distal end comprise an adhesive end formed around said core recess.

24. The flexible driveshaft assembly of claim 22, wherein said plurality of coils extend beyond said first and said second ends of said core for forming said core recess.

25. The flexible driveshaft assembly of claim 14, wherein said proximal end is configured as a drive coupler and said distal end is configured as a tool collet.

26. The flexible driveshaft assembly of claim 14, wherein said flexible driveshaft is configured to be disposable.

27. A flexible driveshaft assembly, comprising:
a proximal coupler and a distal coupler;
a flexible shaft having a proximal end connected to said proximal coupler, a distal end connected to said distal coupler, and a longitudinal axis, said flexible shaft including:
a sleeve;
a core having a first end and a second end, said core being housed within said sleeve; and
a plurality of coils arranged around said core in at least one layer, said plurality of coils in said at least one layer being separated from one another; and
a surgical cutter coupled to the distal coupler and configured to be rotated by the flexible shaft to cut tissue.

28. The flexible driveshaft assembly of claim 27, wherein said core comprises a non-metallic core.

29. The flexible driveshaft assembly of claim 27, wherein said core comprises a hollow core.

30. The flexible driveshaft assembly of claim 27, wherein said plurality of coils are spirally wound around said core and affixed to said proximal coupler and said distal coupler.

31. The flexible driveshaft assembly of claim 27, wherein said plurality of coils are spiral-formed multi-strand fiberglass roving.

32. The flexible driveshaft assembly of claim 27, wherein said plurality of coils are embedded in a polymer matrix.

33. The flexible driveshaft assembly of claim 27, wherein each coil of said plurality of coils is formed of a fiber-reinforced plastic composite.

34. The flexible driveshaft assembly of claim 27, wherein an orientation of said coils relative to said longitudinal axis of said flexible shaft is approximately 45°.

35. The flexible driveshaft assembly of claim 27, wherein said plurality of coils are adhesively bonded to said proximal coupler and to each other at said first end of said core, and to said distal coupler and to each other at said second end of said core.

36. The flexible driveshaft assembly of claim 27, wherein said sleeve is plastic, and wherein said sleeve is shrunk-fit onto said core and said plurality of coils arranged around said core.

37. The flexible driveshaft assembly of claim 27, wherein said proximal coupler and said distal coupler each include a respective mating bore, said first end fitting within said mating bore of said proximal coupler and said second end fitting within said mating bore of said distal coupler.

38. The flexible driveshaft assembly of claim 27, wherein said proximal end of said flexible shaft is removably-connected to said proximal coupler and said distal end of said flexible shaft is removably-connected to said distal coupler.

39. The flexible driveshaft assembly of claim 38, wherein said proximal and distal couplers comprise metal or plastic.

40. The flexible driveshaft assembly of claim 38, wherein said flexible shaft is configured to be disposable.

41. The flexible driveshaft assembly of claim 27, wherein said flexible driveshaft is configured to be disposable, and wherein said proximal and distal couplers comprise molded adhesive couplers.

42. The flexible driveshaft assembly of claim 27, wherein said proximal coupler is configured as a drive coupler and said distal coupler is configured as a tool collet.

* * * * *